(12) United States Patent
Lee et al.

(10) Patent No.: US 10,154,816 B2
(45) Date of Patent: Dec. 18, 2018

(54) ADHESIVE WEARABLE DEVICE

(71) Applicant: Cheng Uei Precision Industry Co., Ltd., New Taipei (TW)

(72) Inventors: James Lee, New Taipei (TW); Kuo Yang Wu, New Taipei (TW); Wen Bing Hsu, New Taipei (TW); Chen Mo Chiang, New Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 695 days.

(21) Appl. No.: 14/828,624

(22) Filed: Aug. 18, 2015

(65) Prior Publication Data
US 2016/0317092 A1  Nov. 3, 2016

(30) Foreign Application Priority Data
Apr. 28, 2015 (TW) ............................ 104206442 U

(51) Int. Cl.
*A61B 5/00* (2006.01)

(52) U.S. Cl.
CPC ........ *A61B 5/6833* (2013.01); *A61B 2562/18* (2013.01)

(58) Field of Classification Search
CPC combination set(s) only.
See application file for complete search history.

(56) References Cited

U.S. PATENT DOCUMENTS

| 2012/0238901 A1* | 9/2012 | Augustine ............ G01K 1/165 600/549 |
| 2015/0257687 A1* | 9/2015 | Pushpala ............ A61B 5/7278 600/345 |

\* cited by examiner

*Primary Examiner* — Scott T Luan
(74) *Attorney, Agent, or Firm* — Lin & Associates Intellectual Property, Inc.

(57) ABSTRACT

An adhesive wearable device includes a cover assembly, a sensor assembly and an electronic module. The cover assembly includes a top cover. The top cover defines an accommodating chamber and a plurality of exhaust holes. The sensor assembly includes a sensor board, and an adhesive pad mounted under the sensor board. The sensor board defines a plurality of through-holes. A bottom surface of the sensor board is equipped with a plurality of sensor units. The adhesive pad defines an opening corresponding to the sensor units, a plurality of perforations and guiding channels extending radially from the opening to the perforations. The electronic module is disposed on and is electrically connected with the sensor board. The cover assembly covers up the sensor assembly and the electronic module. The exhaust holes are communicated with the opening by virtue of the accommodating chamber, the through-holes, the perforations and the guiding channels.

17 Claims, 11 Drawing Sheets

ADHESIVE WEARABLE DEVICE

CROSS-REFERENCE TO RELATED APPLICATION

The present application is based on, and claims priority form, Taiwan Patent Application No. 104206442, filed Apr. 28, 2015, the disclosure of which is hereby incorporated by reference herein in its entirety.

BACKGROUND OF THE INVENTION

1. Field of the Invention

The present invention generally relates to a wearable device, and more particularly to an adhesive wearable device.

2. The Related Art

Generally, a conventional adhesive wearable device is worn on a body of a user. In order to make the user who wears the adhesive wearable device keep daily routines and exercises, a size, weight and volume of the adhesive wearable device are all key considerations of designing the adhesive wearable device. And it also has a lot of limitations in the structure design. The adhesive wearable device need be worn for a long time to contact a skin surface of the body of the user directly, so a comfort consideration is especially important.

When the adhesive wearable device is worn on the skin surface of the body for a long time to contact the skin surface directly, with variations of environmental temperatures, muscle contractions and other different conditions, thermal energies generated by the body are increased to make sweat of the body (sweat evaporated by a normal person in 24 hours is about 600-700 cc).

However, the adhesive wearable device is miniaturized, so the adhesive wearable device usually omits an exhaust structure that makes air of an inside of the adhesive wearable device have no way of being pushed out of the adhesive wearable device to circulate and the sweat be hardly dried. As a result, an adhesive effect of the detachable adhesive wearable device is affected to lower a comfort degree.

SUMMARY OF THE INVENTION

An object of the present invention is to provide an adhesive wearable device detachably adhered to a skin surface of a body. The adhesive wearable device includes a cover assembly and a sensor assembly. The cover assembly includes a top cover, and an adhesive ring mounted under the top cover. The top cover defines an accommodating chamber penetrating through a substantial middle of a bottom surface of the top cover, and a plurality of spaced exhaust holes communicated with the accommodating chamber. The sensor assembly includes a sensor board, and an adhesive pad mounted under the sensor board. The sensor board defines a plurality of spaced through-holes close to a periphery of the sensor board. A bottom surface of the sensor board is equipped with a plurality of sensor units. The adhesive pad defines an opening corresponding to the sensor units of the sensor board. The sensor units are exposed to the opening. The adhesive pad defines a plurality of perforations corresponding to the through-holes and a plurality of guiding channels extending radially from the opening to the perforations. The perforations are communicated with the opening through the guiding channels. The cover assembly covers up the sensor assembly. The exhaust holes of the cover assembly are communicated with the opening of the adhesive pad by virtue of the accommodating chamber of the top cover, the through-holes of the sensor board, the perforations of the adhesive pad and the guiding channels of the adhesive pad.

Another object of the present invention is to provide another adhesive wearable device detachably adhered to a skin surface of a body. The adhesive wearable device includes a cover assembly, a sensor assembly and an electronic module. The cover assembly includes a top cover, and an adhesive ring mounted under the top cover. The top cover defines an accommodating chamber penetrating through a substantial middle of a bottom surface of the top cover, and a plurality of spaced exhaust holes communicated with the accommodating chamber. The sensor assembly includes a sensor board, and an adhesive pad mounted under the sensor board. The sensor board defines a plurality of spaced through-holes close to a periphery of the sensor board. A bottom surface of the sensor board is equipped with a plurality of sensor units. The adhesive pad defines an opening corresponding to the sensor units of the sensor board. The sensor units are exposed to the opening. The adhesive pad defines a plurality of perforations corresponding to the through-holes and a plurality of guiding channels extending radially from the opening to the perforations. The perforations are communicated with the opening through the guiding channels. The electronic module is disposed on the sensor board and is electrically connected with the sensor board. The cover assembly covers up the electronic module and the sensor assembly. The electronic module is assembled in the accommodating chamber of the top cover. The exhaust holes of the cover assembly are communicated with the opening of the adhesive pad by virtue of the accommodating chamber of the top cover, the through-holes of the sensor board, the perforations of the adhesive pad and the guiding channels of the adhesive pad.

As described above, the adhesive wearable device is detachably adhered to the skin surface of the body directly, when a greater pressure of an inside of the adhesive wearable device is generated, air of the inside of the adhesive wearable device is pushed out of the adhesive wearable device through the opening, the guiding channels, the perforations, the through-holes, the accommodating chamber, the exhaust holes, and first waterproof and breathable films or a second waterproof and breathable film to make the air circulate for keeping the pressure balance between the inside of the adhesive wearable device and an outside of the adhesive wearable device, so that the sweat is dried. Therefore, an adhesive effect of the adhesive wearable device is assured to improve a comfort degree.

BRIEF DESCRIPTION OF THE DRAWINGS

The present invention will be apparent to those skilled in the art by reading the following description, with reference to the attached drawings, in which.

DETAILED DESCRIPTION OF THE EMBODIMENT

Figure 1:
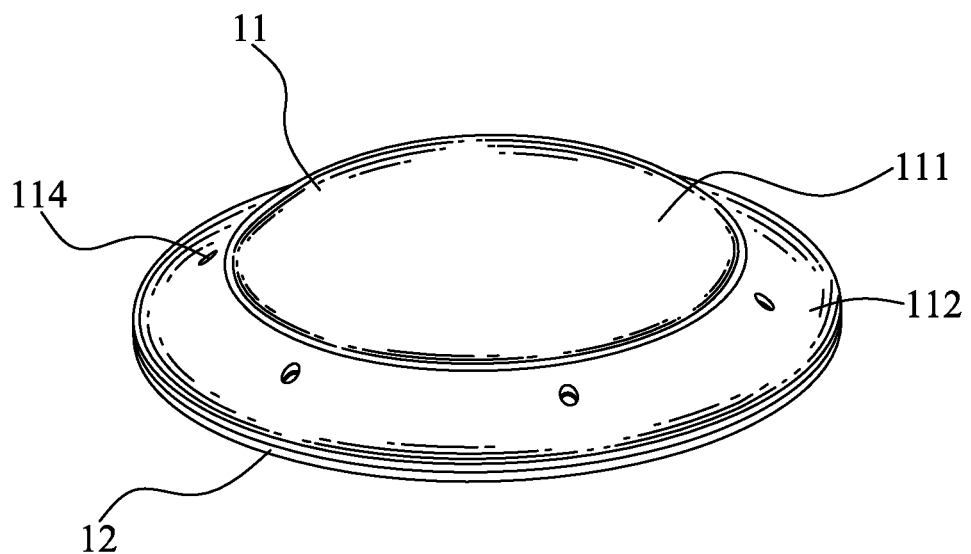
FIG. 1 is a perspective view of an adhesive wearable device in accordance with a first embodiment of the present invention.

Referring to FIG. 1 to FIG. 7, an adhesive wearable device 100 in accordance with a first embodiment of the present invention is shown. The adhesive wearable device 100 in accordance with the first embodiment of the present invention is worn on a body 200, and is detachably adhered to a skin surface 201 of the body 200 directly. The adhesive wearable device 100 includes a cover assembly 10, a sensor assembly 20 and an electronic module 30.

Referring to FIG. 1, FIG. 2, FIG. 5 and FIG. 7, the cover assembly 10 includes a top cover 11, and an adhesive ring 12 mounted under the top cover 11. The top cover 11 defines an accommodating chamber 113 penetrating through a substantial middle of a bottom surface of the top cover 11. The top cover 11 has an arching portion 111 arched outward, and a ring-shaped peripheral portion 112 connected with a periphery of the arching portion 111. An inside of the arching portion 111 forms the accommodating chamber 113. A bottom surface of the peripheral portion 112 is plane. The top cover 11 defines a plurality of spaced exhaust holes 114 communicated with the accommodating chamber 113. Preferably, the exhaust holes 114 are annularly distributed in the top cover 11 for improving breathability performance of the adhesive wearable device 100. Each of the exhaust holes 114 shows a substantial L shape. Each of the exhaust holes 114 includes a first branch 1141 penetrating through the peripheral portion 112 of the top cover 11, and a second branch 1142 extended inward from a bottom of the first branch 1141 and further penetrating through a peripheral sidewall of the accommodating chamber 113. The second branch 1142 of each of the exhaust holes 114 is communicated with the accommodating chamber 113. An inner periphery of a bottom of the peripheral sidewall of the accommodating chamber 113 is recessed inward to form a fastening groove 115 communicated with the accommodating chamber 113. The adhesive ring 12 is of a ring shape. The adhesive ring 12 is mounted to the bottom surface of the peripheral portion 112 of the top cover 11. An external diameter of the adhesive ring 12 is equal to an external diameter of the peripheral portion 112 of the top cover 11.

Figure 2:
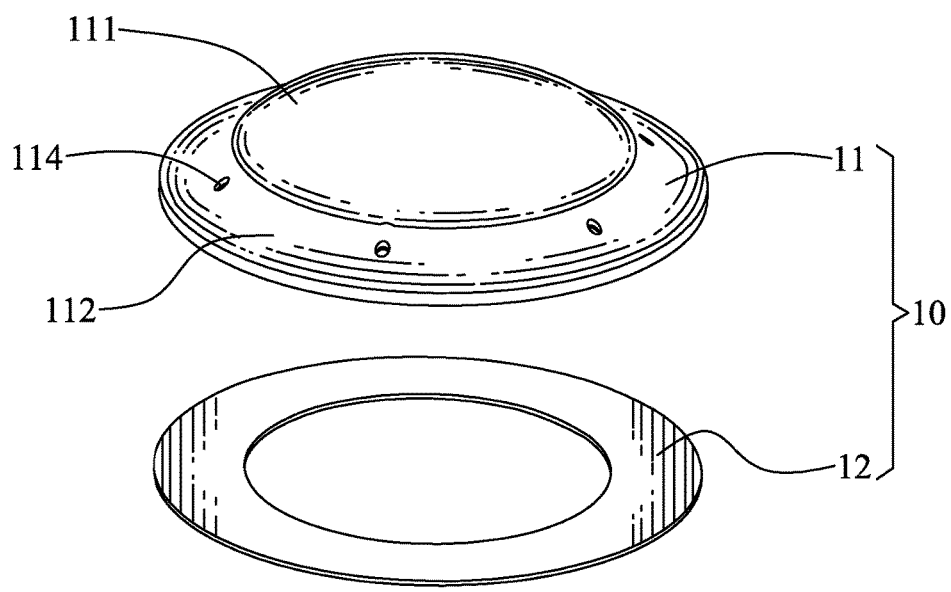
FIG. 2 is a partially exploded view of the adhesive wearable device of FIG. 1.
Figure 2:
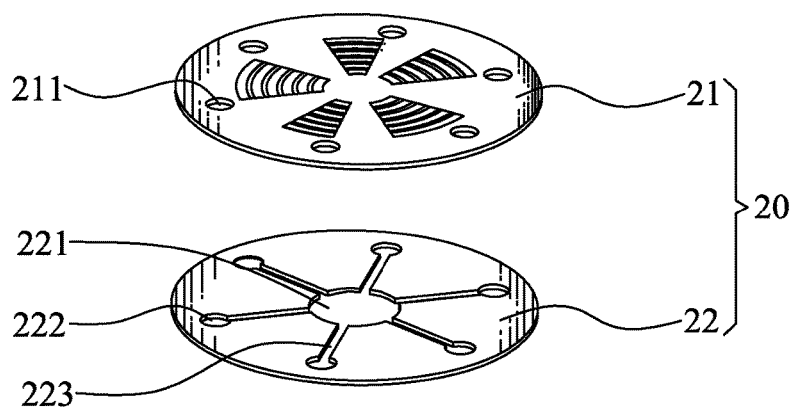
Figure 7:
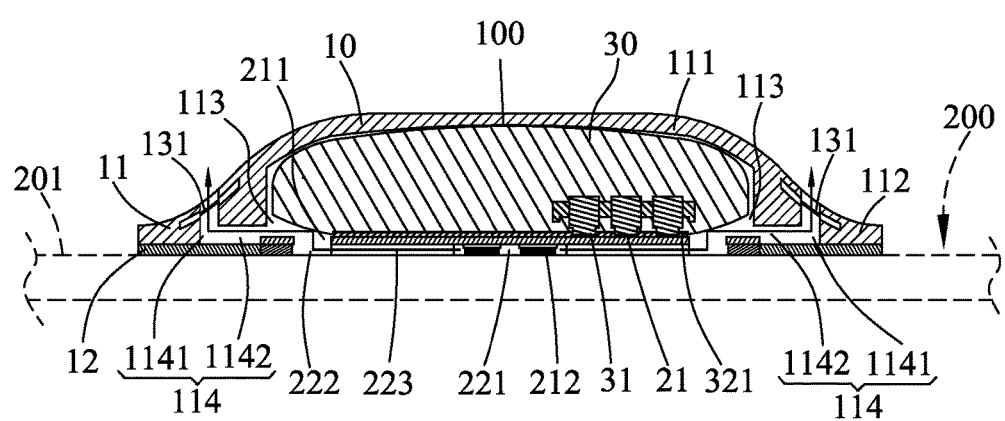
FIG. 7 is a schematic diagram showing that the adhesive wearable device in accordance with the first embodiment of the present invention contacts a skin surface.
Figure 8:
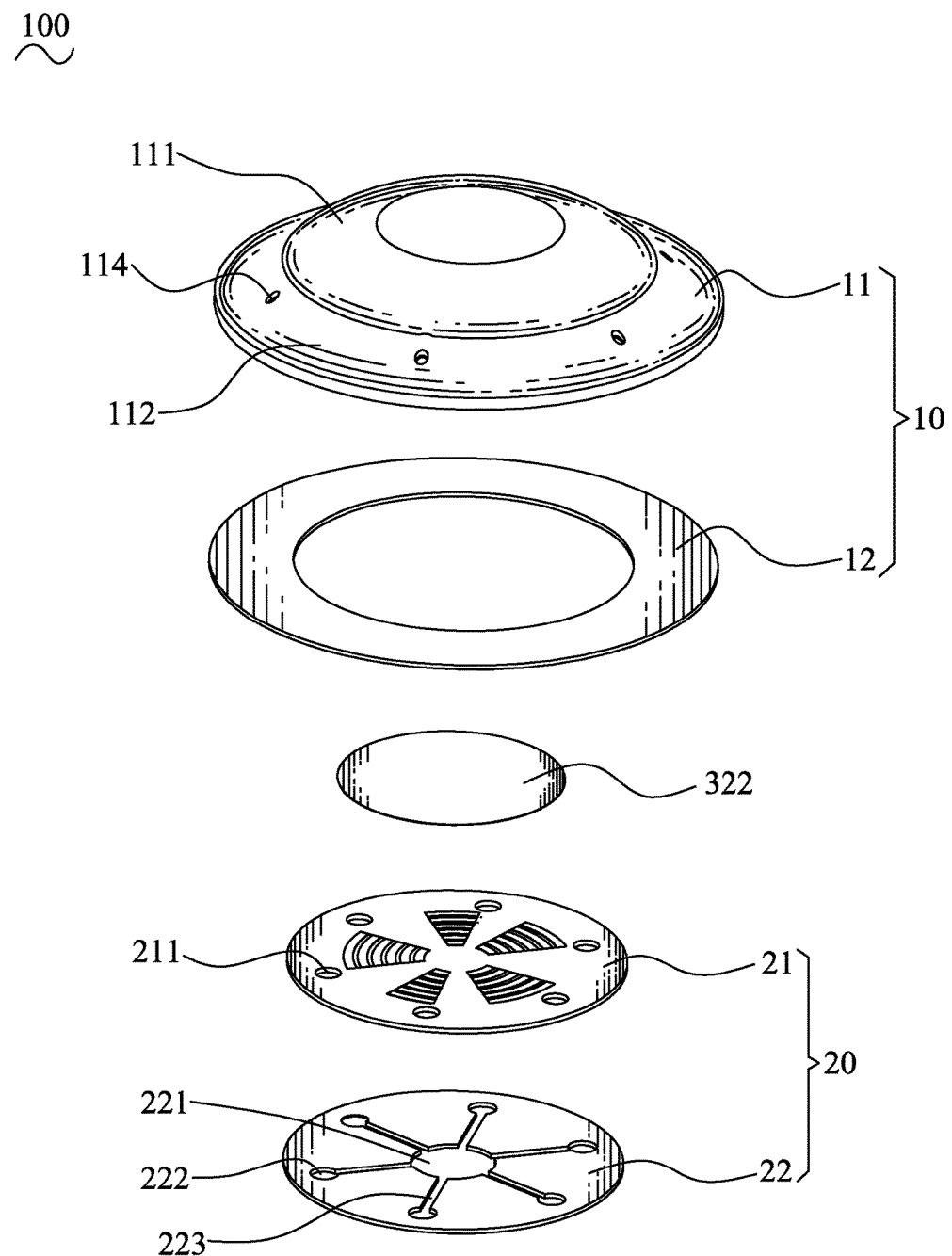
FIG. 8 is a partially exploded view of an adhesive wearable device in accordance with a second embodiment of the present invention.
Figure 9:
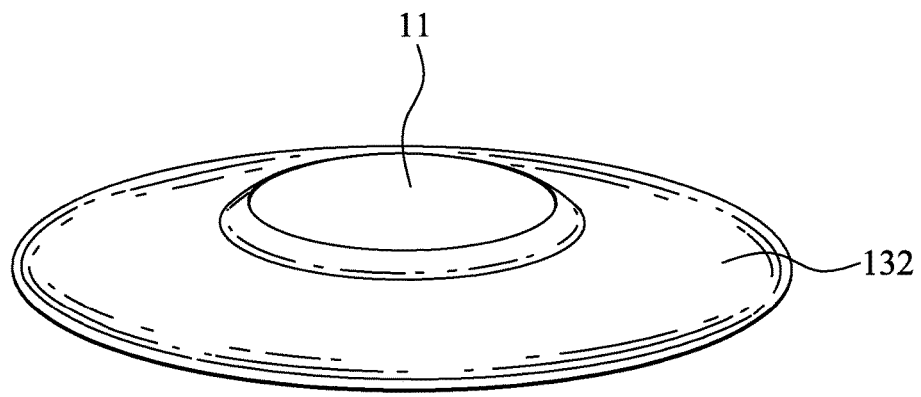
FIG. 9 is a perspective view of an adhesive wearable device in accordance with a third embodiment of the present invention.
Figure 10:
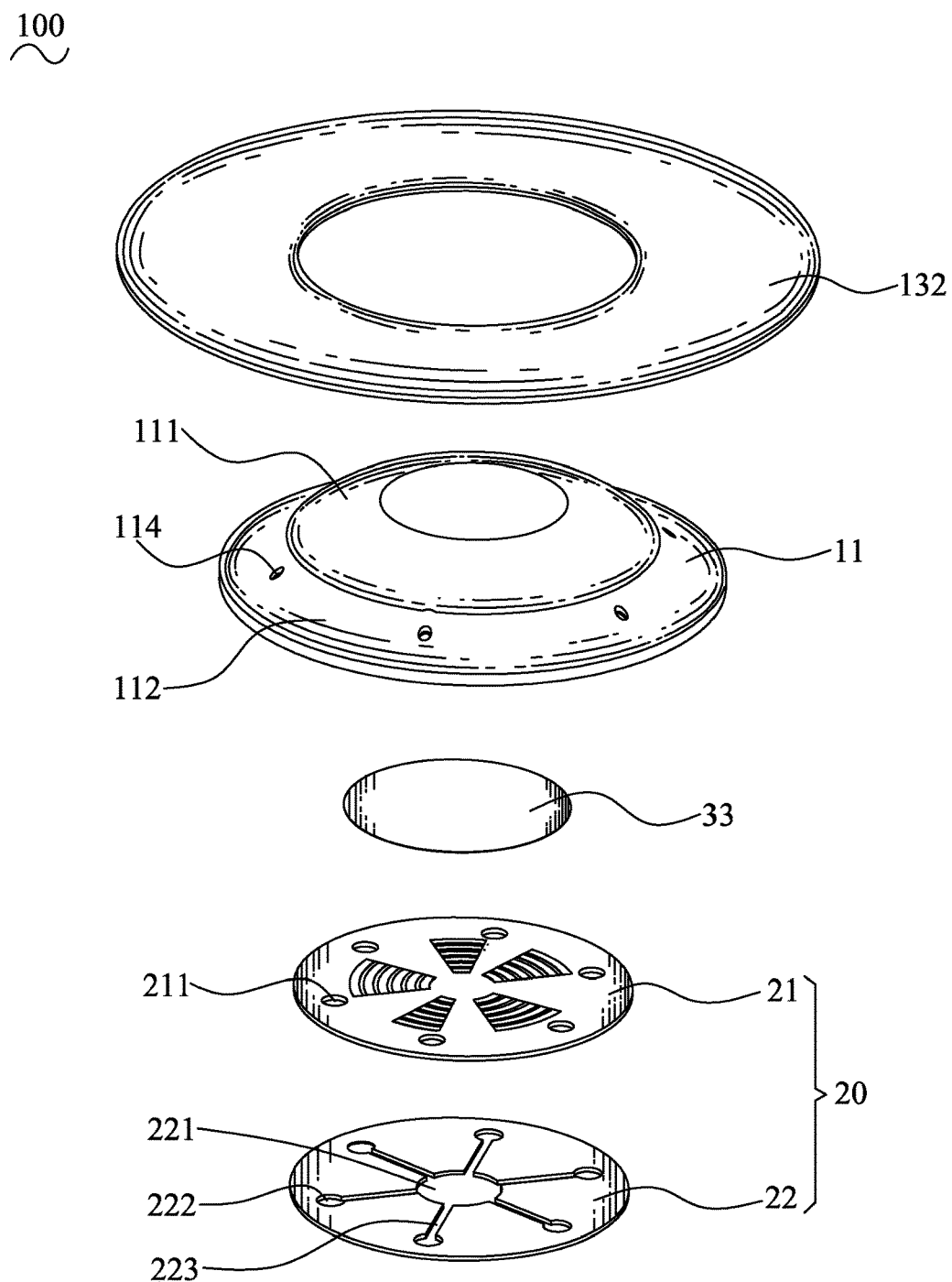
FIG. 10 is a partially exploded view of the adhesive wearable device of FIG. 9.
Figure 11:
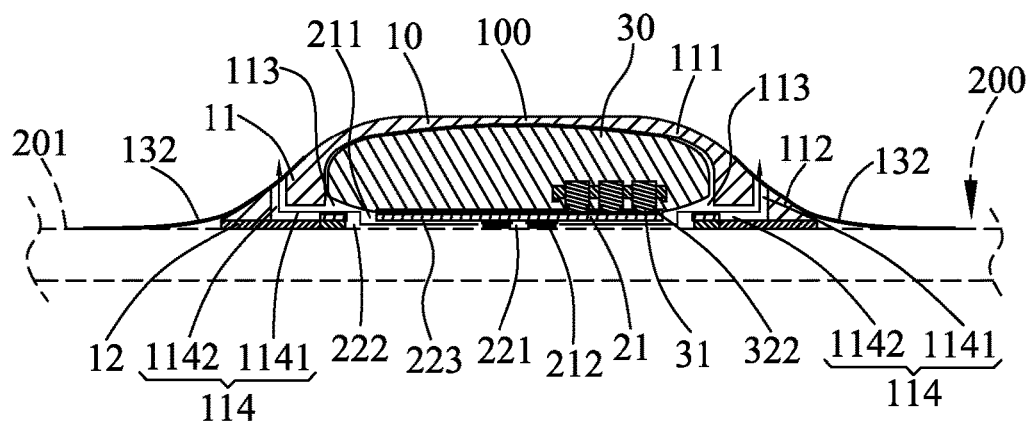
FIG. 11 is a schematic diagram showing that the adhesive wearable device in accordance with the third embodiment contacts the skin surface.

Referring to FIG. 1, FIG. 2 and FIG. 7, the cover assembly 10 further includes a plurality of first waterproof and breathable films 131. The first waterproof and breathable films 131 are correspondingly assembled in the exhaust holes 114 of the top cover 11. When pressures of insides of the first waterproof and breathable films 131 are higher than pressures of outsides of the first waterproof and breathable films 131, air is pushed out of the adhesive wearable device 100 through the first waterproof and breathable films 131, so the air circulates from the insides of the first waterproof and breathable films 131 to the outsides of the first waterproof and breathable films 131. Simultaneously, each of the first waterproof and breathable films 131 has a waterproof function to prevent moisture entering the accommodating chamber 113 of the top cover 11.

Figure 3:
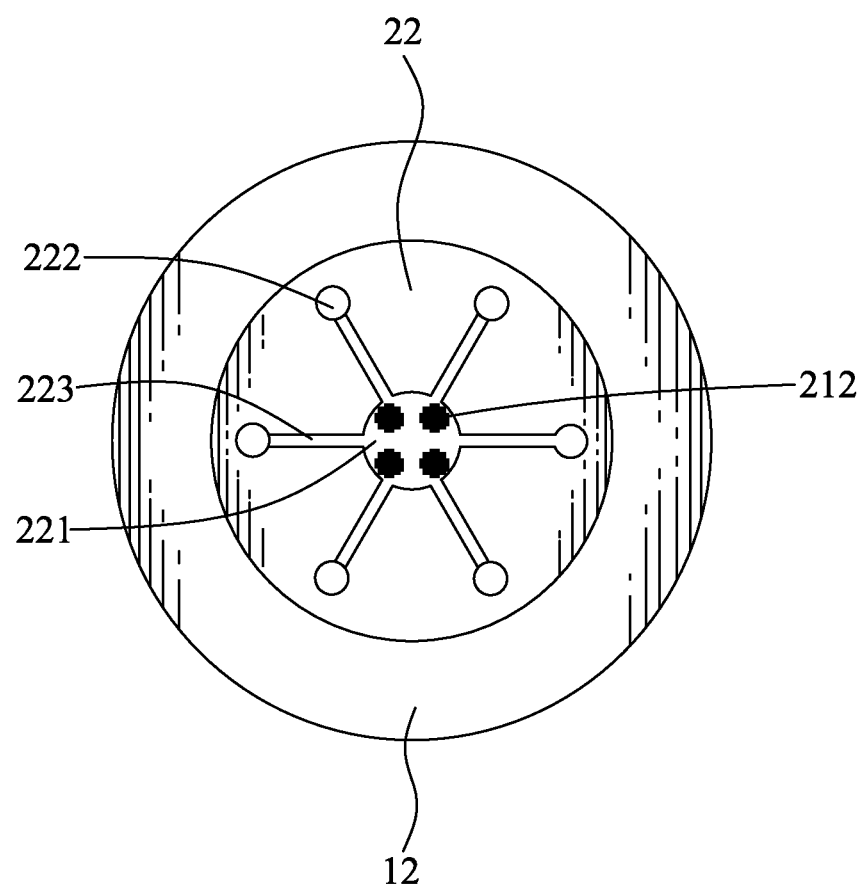
FIG. 3 is a bottom view of the adhesive wearable device of FIG. 1.

Referring to FIG. 2 and FIG. 3, the sensor assembly 20 includes a sensor board 21 and an adhesive pad 22. The sensor board 21 is of a circular shape. A diameter of the sensor board 21 is equal to an internal diameter of the adhesive ring 12. The sensor board 21 defines a plurality of spaced through-holes 211 close to a periphery of the sensor board 21. Preferably, the through-holes 211 are annularly distributed in the sensor board 21 and separately corresponding to the exhaust holes 114 for improving the breathability performance of the adhesive wearable device 100. A middle of a bottom surface of the sensor board 21 is equipped with a plurality of sensor units 212.

Referring to FIG. 2 and FIG. 3, the adhesive pad 22 is mounted under the sensor board 21. The adhesive pad 22 is of a circular shape. A diameter of the adhesive pad 22 is equal to the diameter of the sensor board 21. A middle of the adhesive pad 22 defines an opening 221 corresponding to the sensor units 212 of the sensor board 21. The sensor units 212 are exposed to the opening 221. The adhesive pad 22 defines a plurality of spaced perforations 222 corresponding to the through-holes 211 of the sensor board 21 and a plurality of guiding channels 223 extending radially from the opening 221 to the perforations 222. The perforations 222 are communicated with the opening 221 through the guiding channels 223. Preferably, the perforations 222 are annularly distributed in the adhesive pad 22 for improving the breathability performance of the adhesive wearable device 100.

Figure 4:
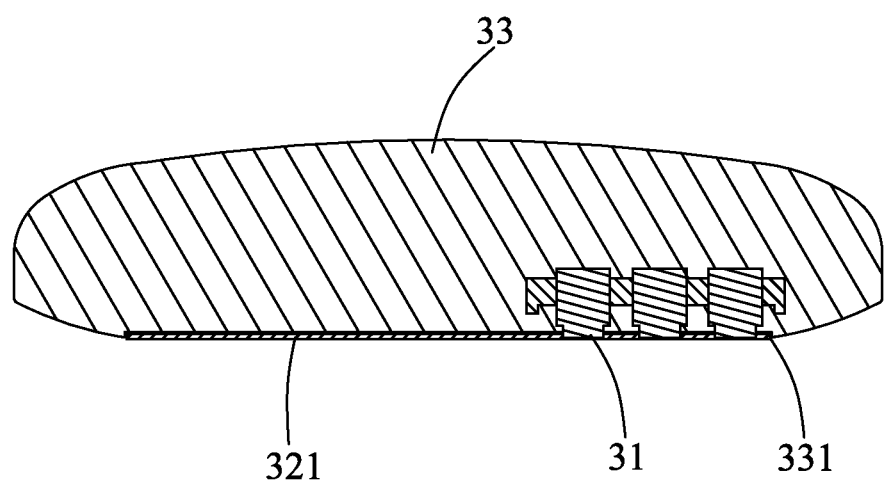
FIG. 4 is a sectional view of an electronic module of the adhesive wearable device of FIG. 1.
Figure 5:
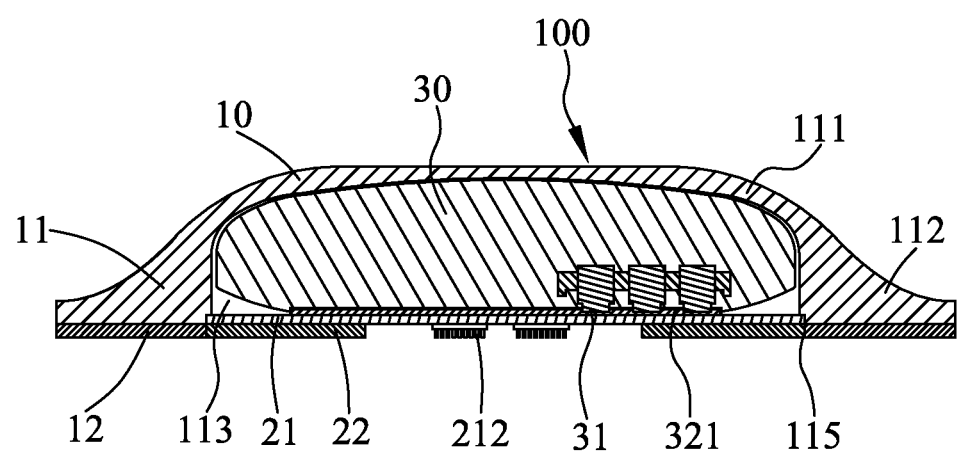
FIG. 5 is a sectional view of the adhesive wearable device of FIG. 1.
Figure 6:
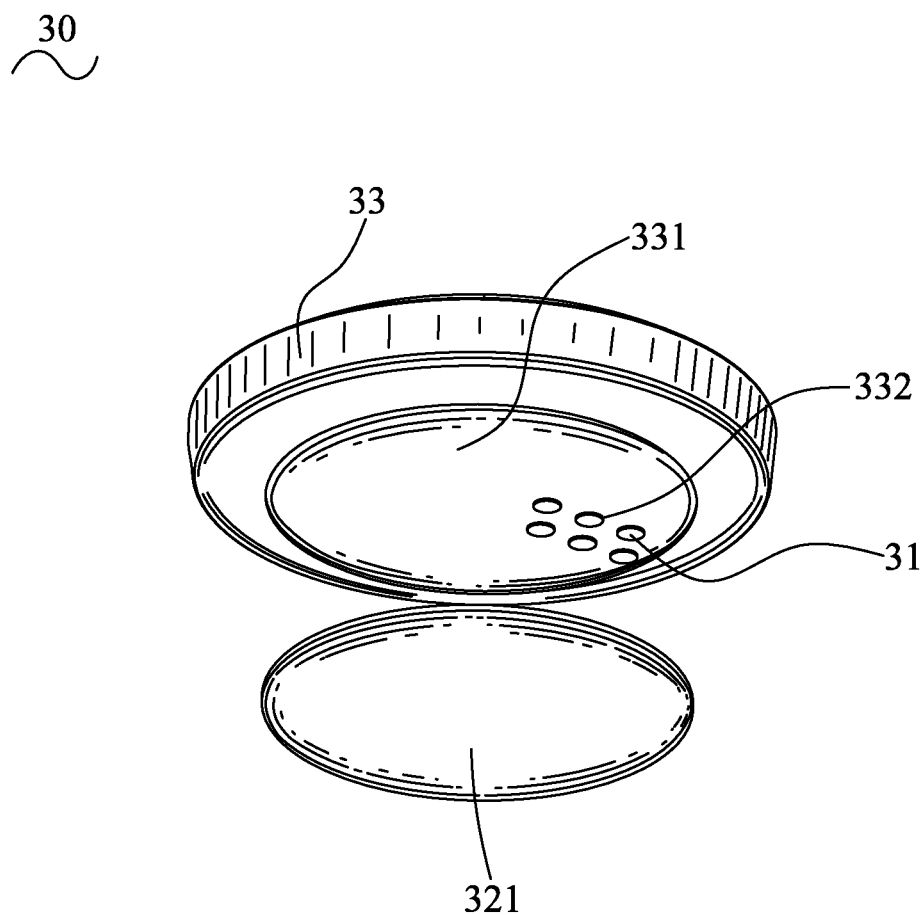
FIG. 6 is a partially exploded view of the electronic module of the adhesive wearable device of FIG. 5.

Referring to FIG. 4, FIG. 5 and FIG. 6, the electronic module 30 shows a circular shape seen from a vertical view. A diameter of the electronic module 30 is substantially equal to a diameter of the sensor board 21 of the sensor assembly 20. The electronic module 30 includes an outer housing 33, a plurality of contact terminals 31 and an anisotropic conductive adhesive 321. Bottom surfaces of the contact terminals 31 are plane. A middle of a bottom of the outer housing 33 is recessed inward to form a receiving cavity 331. An inner wall of the receiving cavity 331 defines a plurality of locating holes 332 communicated with the receiving cavity 331.

Referring to FIG. 4, FIG. 5 and FIG. 6 again, the contact terminals 31 are disposed to the outer housing 33. The contact terminals 31 are located to the locating holes 332 with the bottom surfaces of the contact terminals 31 being exposed to the receiving cavity 331 through the locating holes 332. The anisotropic conductive adhesive 321 is received in the receiving cavity 331 and adhered to the inner wall of the receiving cavity 331. The anisotropic conductive adhesive 321 electrically contacts the bottom surfaces of the contact terminals 31.

Referring to FIG. 1 to FIG. 7, when the adhesive wearable device 100 is assembled, the electronic module 30 is disposed on the sensor board 21. The sensor board 21 of the sensor assembly 20 is adhered to a bottom surface of the anisotropic conductive adhesive 321. The electronic module 30 is electrically connected with the sensor board 21 by the anisotropic conductive adhesive 321. The anisotropic conductive adhesive 321 has a compressibility performance for making the anisotropic conductive adhesive 321 completely contact the bottom surfaces of the contact terminals 31. So, the anisotropic conductive adhesive 321 cooperates with the contact terminals 31 to ensure a contact stability, uniformity and symmetry between the electronic module 30 and the sensor board 21. The cover assembly 10 covers up the electronic module 30 and the sensor assembly 20. The electronic module 30 is assembled in the accommodating chamber 113 of the top cover 11. The sensor board 21 of the sensor assembly 20 passes through the adhesive ring 12 and is fastened in the fastening groove 115. The adhesive pad 22 of the sensor assembly 20 is located in the adhesive ring 12. The exhaust holes 114 of the cover assembly 10 are communicated with the opening 221 of the adhesive pad 22 by virtue of the accommodating chamber 113, the through-holes 211 of the sensor board 21, the perforations 222 of the adhesive pad 22 and the guiding channels 223 of the adhesive pad 22.

Referring to FIG. 1 to FIG. 8, an adhesive wearable device 100 in accordance with a second embodiment of the present invention is shown. Differences between the first embodiment and the second embodiment of the adhesive wearable device 100 are described as follows. In the second embodiment, the electronic module 30 includes a double-sided pressure sensing adhesive 322 for replacing the anisotropic conductive adhesive 321 of the adhesive wearable device 100 in accordance with the first embodiment. A top surface and a bottom surface of the double-sided pressure sensing adhesive 322 are adhered with two pieces of release paper, respectively. In assembly, the piece of release paper adhered to the bottom surface of the double-sided pressure sensing adhesive 322 is peeled off, the bottom surface of the double-sided pressure sensing adhesive 322 is adhered to a top surface of the sensor board 21. Then the piece of release paper adhered to the top surface of the double-sided pressure sensing adhesive 322 is peeled off, the outer housing 33 together with the contact terminals 31 of the electronic module 30 is mounted on the top surface of the double-sided pressure sensing adhesive 322 directly. Specifically, the double-sided pressure sensing adhesive 322 is received in the receiving cavity 331. The double-sided pressure sensing adhesive 322 electrically contacts the bottom surfaces of the contact terminals 31. So the electronic module 30 is electrically connected with sensor board 21 by the double-sided pressure sensing adhesive 322.

Referring to FIG. 7 to FIG. 11, an adhesive wearable device 100 in accordance with a third embodiment of the present invention is shown. The adhesive wearable device 100 in accordance with the third embodiment is worn on the body 200, and is detachably adhered to the skin surface 201 of the body 200 directly. Differences between the first embodiment and the third embodiment of the adhesive wearable device 100 are described as follows. The adhesive wearable device 100 in accordance with the third embodiment includes a second waterproof and breathable film 132 for replacing the first waterproof and breathable films 131. The second waterproof and breathable film 132 is of a ring shape seen from a vertical view. The second waterproof and breathable film 132 is covered on the peripheral portion 112 of the top cover 11 and seals up the exhaust holes 114 of the top cover 11.

Referring to FIG. 1 to FIG. 8, in use, the adhesive wearable device 100 in accordance with the present invention is worn on the body 200, and is detachably adhered to the skin surface 201 of the body 200. The adhesive ring 12 of the cover assembly 10, the adhesive pad 22 of the sensor assembly 20 and the sensor units 212 of the sensor assembly 20 are adhered to the skin surface 201 of the body 200. The sensor units 212 measure signals through the skin surface 201, and send the measured signals to the electronic module 30 through the sensor board 21 and the anisotropic conductive adhesive 321. The electronic module 30 is connected with a personal mobile device (not shown) to read the measured signals by virtue of low-power Bluetooth technology.

Referring to FIG. 1 to FIG. 8 again, because the adhesive wearable device 100 needs be worn for a long time and contacts the skin surface 201 directly, with variations of environmental temperatures, muscle contractions and other conditions, sweat of the body 200, the greater pressure is generated in the inside of the adhesive wearable device 100. When a greater pressure of the inside of the adhesive wearable device 100 is generated, the air of the inside of the adhesive wearable device 100 is pushed out of the adhesive wearable device 100 through the opening 221, the guiding channels 223, the perforations 222, the through-holes 211, the accommodating chamber 113, the exhaust holes 114, and the first waterproof and breathable films 131 or the second waterproof and breathable film 132 (shown as pointing directions by arrows) to make the air circulate for keeping a pressure balance between the inside of the adhesive wearable device 100 and an outside of the adhesive wearable device 100.

As described above, the adhesive wearable device 100 is detachably adhered to the skin surface 201 of the body 200 directly, when the greater pressure of the inside of the adhesive wearable device 100 is generated, the air of the inside of the adhesive wearable device 100 is pushed out of the adhesive wearable device 100 through the opening 221, the guiding channels 223, the perforations 222, the through-holes 211, the accommodating chamber 113, the exhaust holes 114, and the first waterproof and breathable films 131 or the second waterproof and breathable film 132 to make the air circulate for keeping the pressure balance between the inside of the adhesive wearable device 100 and the outside of the adhesive wearable device 100, so that the sweat is dried. Therefore, an adhesive effect of the adhesive wearable device 100 is assured to improve a comfort degree.

What is claimed is:

1. An adhesive wearable device detachably adhered to a skin surface of a body, comprising:
   a cover assembly including a top cover, an adhesive ring mounted under the top cover and a plurality of first waterproof and breathable films, the top cover defining an accommodating chamber penetrating through a substantial middle of a bottom surface of the top cover, and a plurality of spaced exhaust holes communicated with the accommodating chamber, the first waterproof and breathable films being correspondingly assembled in the exhaust holes; and
   a sensor assembly including a sensor board, and an adhesive pad mounted under the sensor board, the sensor board defining a plurality of spaced through-holes close to a periphery of the sensor board, a bottom surface of the sensor board being equipped with a plurality of sensor units, the adhesive pad defining an opening corresponding to the sensor units of the sensor board, the sensor units being exposed to the opening, the adhesive pad defining a plurality of perforations corresponding to the through-holes and a plurality of guiding channels extending radially from the opening to the perforations, the perforations being communicated with the opening through the guiding channels,
   wherein the cover assembly covers up the sensor assembly, and the exhaust holes of the cover assembly are communicated with the opening of the adhesive pad by virtue of the accommodating chamber of the top cover, the through-holes of the sensor board, the perforations of the adhesive pad and the guiding channels of the adhesive pad.

2. The adhesive wearable device as claimed in claim 1, wherein the cover assembly includes a second waterproof and breathable film of a ring shape, and the second waterproof and breathable film is covered on the peripheral portion of the top cover and seals up the exhaust holes of the top cover.

3. The adhesive wearable device as claimed in claim 1, wherein the sensor board shows a circular shape, and a diameter of the sensor board is equal to an internal diameter of the adhesive ring.

4. The adhesive wearable device as claimed in claim 1, wherein the top cover has an arching portion arched outward, and a ring-shaped peripheral portion connected with a periphery of the arching portion, an inside of the arching portion forms the accommodating chamber, a bottom surface of the peripheral portion is plane, each of the exhaust holes shows a substantial L shape, each of the exhaust holes includes a first branch penetrating through the peripheral portion of the top cover, and a second branch extended inward from a bottom of the first branch and further penetrating through a peripheral sidewall of the accommodating chamber, and the second branch of each of the exhaust holes is communicated with the accommodating chamber.

5. The adhesive wearable device as claimed in claim 4, wherein an external diameter of the adhesive ring is equal to an external diameter of the peripheral portion of the top cover.

6. The adhesive wearable device as claimed in claim 1, wherein an inner periphery of a bottom of a peripheral sidewall of the accommodating chamber is recessed inward to form a fastening groove communicated with the accommodating chamber, the sensor board of the sensor assembly passes through the adhesive ring and is fastened in the fastening groove, and the adhesive pad of the sensor assembly is located in the adhesive ring.

7. The adhesive wearable device as claimed in claim 1, wherein the exhaust holes are annularly distributed in the top cover, the through-holes are annularly distributed in the sensor board and separately corresponding to the exhaust holes, and the perforations are annularly distributed in the adhesive pad for improving breathability performance of the adhesive wearable device.

8. An adhesive wearable device detachably adhered to a skin surface of a body, comprising:
a cover assembly including a top cover, an adhesive ring mounted under the top cover and a plurality of first waterproof and breathable films, the top cover defining an accommodating chamber penetrating through a substantial middle of a bottom surface of the top cover, and a plurality of spaced exhaust holes communicated with the accommodating chamber, the first waterproof and breathable films being correspondingly assembled in the exhaust holes;
a sensor assembly including a sensor board, and an adhesive pad mounted under the sensor board, the sensor board defining a plurality of spaced through-holes close to a periphery of the sensor board, a bottom surface of the sensor board being equipped with a plurality of sensor units, the adhesive pad defining an opening corresponding to the sensor units of the sensor board, the sensor units being exposed to the opening, the adhesive pad defining a plurality of perforations corresponding to the through-holes and a plurality of guiding channels extending radially from the opening to the perforations, the perforations being communicated with the opening through the guiding channels; and
an electronic module disposed on the sensor board and electrically connected with the sensor board,
wherein the cover assembly covers up the electronic module and the sensor assembly, the electronic module is assembled in the accommodating chamber of the top cover, and the exhaust holes of the cover assembly are communicated with the opening of the adhesive pad by virtue of the accommodating chamber of the top cover, the through-holes of the sensor board, the perforations of the adhesive pad and the guiding channels of the adhesive pad.

9. The adhesive wearable device as claimed in claim 8, wherein the cover assembly includes a second waterproof and breathable film of a ring shape, and the second waterproof and breathable film is covered on the peripheral portion of the top cover and seals up the exhaust holes of the top cover.

10. The adhesive wearable device as claimed in claim 8, wherein the sensor board shows a circular shape, and a diameter of the sensor board is equal to an internal diameter of the adhesive ring.

11. The adhesive wearable device as claimed in claim 8, wherein the top cover has an arching portion arched outward, and a ring-shaped peripheral portion connected with a periphery of the arching portion, an inside of the arching portion forms the accommodating chamber, a bottom surface of the peripheral portion is plane, each of the exhaust holes shows a substantial L shape, each of the exhaust holes includes a first branch penetrating through the peripheral portion of the top cover, and a second branch extended inward from a bottom of the first branch and further penetrating through a peripheral sidewall of the accommodating chamber, and the second branch of each of the exhaust holes is communicated with the accommodating chamber.

12. The adhesive wearable device as claimed in claim 11, wherein an external diameter of the adhesive ring is equal to an external diameter of the peripheral portion of the top cover.

13. The adhesive wearable device as claimed in claim 8, wherein the electronic module shows a circular shape, and a diameter of the electronic module is substantially equal to a diameter of the sensor board of the sensor assembly.

14. The adhesive wearable device as claimed in claim 8, wherein an inner periphery of a bottom of a peripheral sidewall of the accommodating chamber is recessed inward to form a fastening groove communicated with the accommodating chamber, the sensor board of the sensor assembly passes through the adhesive ring and is fastened in the fastening groove, and the adhesive pad of the sensor assembly is located in the adhesive ring.

15. The adhesive wearable device as claimed in claim 8, wherein the electronic module includes an outer housing, a plurality of contact terminals and an anisotropic conductive adhesive, bottom surfaces of the contact terminals are plane, a middle of a bottom of the outer housing is recessed inward to form a receiving cavity, an inner wall of the receiving cavity defines a plurality of locating holes communicated with the receiving cavity, the contact terminals are located to the locating holes with the bottom surfaces of the contact terminals being exposed to the receiving cavity through the locating holes, the anisotropic conductive adhesive is received in the receiving cavity and adhered to the inner wall of the receiving cavity, the anisotropic conductive adhesive electrically contacts the bottom surfaces of the contact terminals, and the electronic module is electrically connected with the sensor board by the anisotropic conductive adhesive.

16. The adhesive wearable device as claimed in claim 8, wherein the electronic module includes an outer housing, a plurality of contact terminals and a double-sided pressure sensing adhesive, bottom surfaces of the contact terminals are plane, a middle of a bottom of the outer housing is recessed inward to form a receiving cavity, an inner wall of the receiving cavity defines a plurality of locating holes communicated with the receiving cavity, the contact terminals are located to the locating holes with the bottom surfaces of contact terminals being exposed to the receiving cavity through the locating holes, a bottom surface of the double-sided pressure sensing adhesive is adhered to a top surface of the sensor board, the double-sided pressure sensing adhesive is received in the receiving cavity and adhered to the inner wall of the receiving cavity, the double-sided pressure sensing adhesive electrically contacts the bottom surfaces of the contact terminals, and the electronic module is electrically connected with sensor board by the double-sided pressure sensing adhesive.

17. The adhesive wearable device as claimed in claim 8, wherein the exhaust holes are annularly distributed in the top cover, the through-holes are annularly distributed in the sensor board and separately corresponding to the exhaust holes, and the perforations are annularly distributed in the adhesive pad for improving breathability performance of the adhesive wearable device.

\* \* \* \* \*